United States Patent [19]

Hammond et al.

[11] 4,443,600

[45] Apr. 17, 1984

[54] SURFACTANT WASHING OF POLYCHLOROISOCYANURIC ACIDS

[75] Inventors: Wayne H. Hammond; George V. Jones, both of Lake Charles, La.

[73] Assignee: Olin Corporation, New Haven, Conn.

[21] Appl. No.: 395,181

[22] Filed: Jul. 6, 1982

[51] Int. Cl.$^3$ .......................................... C07D 251/36
[52] U.S. Cl. .................................................... 544/190
[58] Field of Search ........................................ 544/190

[56] References Cited

U.S. PATENT DOCUMENTS 3,142,647 7/1964 Glasgow .............................. 252/187
4,220,768 9/1980 Wojtowicz et al. ................ 544/190

Primary Examiner—John M. Ford
Attorney, Agent, or Firm—Arthur E. Oaks; Donald F. Clements

[57] ABSTRACT

A process for the production of a polychloroisocyanuric acid filter cake having reduced moisture and salt content leading to quicker drying and a purer product is disclosed. Such a result is achieved by the addition of between about 50 and about 500 ppm of a suitable surfactant wetting agent to the water used to wash the cake after it is filtered from the reaction mass. Preferred surfactant wetting agents are alkoxylated alkyl alcohols and sodium dialkyl sulfosuccinates.

10 Claims, No Drawings

SURFACTANT WASHING OF POLYCHLOROISOCYANURIC ACIDS

This invention relates to a process for preparing chlorinated cyanuric acid having lower residual water and salt contents than previously known materials. Polychloroisocyanurates are well-known products used in washings, bleaching and sanitizing applications.

In a process for the production of polychloroisocyanuric acid products described by Wojtowicz et al. in U.S. Pat. No. 4,220,768, said patent being incorporated herein by reference, the reaction mixture includes a cyanuric compound. Suitable cyanuric compounds include alkali metal cyanurates, alkaline earth metal cyanurates and cyanuric acid. Alkali metal cyanurates include those in which the alkali metal is sodium or potassium and the cyanuric compound is monosodium or monopotassium cyanurate, disodium or dipotassium cyanurate, or trisodium or tripotassium cyanurate. Alkaline earth metal cyanurates which may be employed include calcium cyanurate or magnesium cyanurate. Where cyanuric acid is used as the cyanuric compound, the reaction mixture also contains an alkali metal hydroxide such as sodium hydroxide or potassium hydroxide or an alkaline earth metal hydroxide such as calcium hydroxide or magnesium hydroxide. These are added in amounts sufficient to neutralize the hydrochloric acid produced during the reaction of the chlorine gas with the cyanuric acid and result in the formation of a certain amount of salt product in the reaction mix.

Chlorine gas is introduced into the reaction mixture in amounts sufficient to produce a polychloroisocyanuric acid such as dichloroisocyanuric acid, trichloroisocyanuric acid or mixtures of the two. Chlorine gas may be the sole chlorinating agent or may be supplemented by additions to the reaction mixture of other chlorinating agents such as hypochlorous acid or hypochlorites. Required amounts or ratios of chlorinating agents and the cyanuric compound to produce polychloroisocyanuric acids are known and described, for example, in U.S. Pat. No. 3,757,018 issued Sept. 4, 1973 to R. N. Mesiah; U.S. Pat. No. 3,810,982 issued May 14, 1974 to R. N. Mesiah; U.S. Pat. No. 3,835,134 issued Sept. 10, 1974 to H. W. Schiessl, D. L. Sawhill and S. K. Bhutani; U.S. Pat. No. 3,835,135 issued Dec. 10, 1974 to D. L. Sawhill; and U.S. Pat. No. 4,220,768 issued Sept. 2, 1980 to J. A. Wojtowicz and M. Scardera.

In the above processes, chlorine gas is continuously introduced into the reaction mixture to chlorinate the cyanuric compound. The reaction mixture is agitated to provide improved contact between the chlorine gas and cyanuric compound. As the reaction proceeds, foam or froth is produced in which particles of the polychloroisocyanuric acid product are thought to be suspended in bubbles of chlorine gas. Small particles of polychloroisocyanuric acid produced by these processes are difficult to filter, and when dried, form a large proportion of fines into the final product.

To circumvent this problem, a suitable foam depressant is added to the reaction mix to produce a polychloroisocyanuric acid product having improved filterability, increased particle sizes, and a lower proportion of fines in the dry product. Suitable foam depressants for this purpose include ethylene oxide terminated alkoxylated alcohols having a cloudpoint up to about 50° C. Examples of these non-ionic foam depressants include ethoxylated alcohols of the following formula:

$$R-(O-CH_2-CH_2)_x-O-H$$

where R represents an alcohol having an aliphatic chain with about 10 to about 18 carbon atoms and x represents a number from about 1 to about 7. Alcohols which may be employed to provide the aliphatic group are primary, secondary and tertiary alcohols and thus may present straight or branched chains of carbon atoms. Examples of suitable alcohols include ethyloctanol, decanol, isodecanol, undecanol, dodecanol, isododecanol, methyldodecanol, tridecanol, tetradecanol, pentadecanol, hexadecanol, heptadecanol, and octadecanol.

Other suitable foam depressants for this use are non-ionic alkoxylated alcohols having the formula:

$$AO-(CH_2-\underset{A'}{CH}-O)_y-(CH_2-CH_2-O)_x-H$$

where A represents a substantially linear hydrocarbon, and more particularly an alkyl group having an average from about 6 to about 10 carbon atoms; A' represents methyl or ethyl, preferably methyl; y represents a number from 0 to about 8 and preferably from about 0 to about 4; and x represents a number from about 1 to about 9 and preferably from about 4 to about 7, with the proviso that where A is greater than 10, y is greater than 0.

The A group is derived from a linear alcohol and generally from a mixture of alcohols. Due to the nature of the process by which these alcohols are prepared, there may be small amounts of branched chain alcohols present. Generally, the presence of such branched chain alcohols in amounts less than about 15 percent of the total alcohol content by weight will not adversely affect the foam depressant properties of the final product.

Cloudpoints of these non-ionic foam depressants are no higher than about 50°. The cloudpoint may be determined by any suitable method such as American Society for Testing Materials Method D2024-65, cloudpoint for non-ionic surfactants.

In addition, suitable as foam depressants are anionic alkali metal salts of esters of dicarboxylic acids having the formula:

$$\underset{AOC-CH-(CH_2)_n-CH-COB}{\overset{O\ \ Z\ \ \ \ \ \ \ \ \ \ \ \ Z'\ \ O}{\|\ \ |\ \ \ \ \ \ \ \ \ \ \ \ \ |\ \ \|}}$$

where A is as defined above; B represents A or an alkali metal; Z and Z' are independently selected from the group consisting of H, SO$_3$H, or SO$_3$M; M represents an alkali metal; n is 0 or 1; with the proviso that where B is A, Z is SO$_3$M and where Z and Z' are H or SO$_3$H, B is an alkali metal.

Suitable as anionic foam depressants of this type are alkali metal salts of monoesters of succinic acid or glutaric acid including hexyl, heptyl, octyl, nonyl, and decyl esters. Also suitable are alkali metal sulfonated diesters of succinic acid or glutaric acid such as dihexyl, diheptyl, dioctyl, dinonyl and didecyl, with dihexyl, dioctyl, and didecyl being preferred. While any alkali metal may be used to form the salts, preferred alkali metals are sodium or potassium.

These materials may be employed in any suitable amounts, such as amounts from about 5 to about 500 with about 20 to about 150 parts per million by weight of the reaction mixture being preferred. It is found that when this is done, it effectively inhibits the chlorine gas bubbles from removing solid particles of polychloroisocyanuric acid from the aqueous medium and producing undesired foam or froth. Particles thus remain in the aqueous medium where they have an opportunity to form larger crystal and solids which reduces the fines content of the final product.

This technique is particularly applicable to processes for the production of polychloroisocyanuric acid such as those of U.S. Pat. Nos. 3,835,134 and 3,835,135, referred to hereinabove. In these processes, an excess of chlorine gas may be used to remove from the reaction mixture any gaseous byproducts such as nitrogen trichloride which may be formed during the reaction period. The reaction mixture thus includes an aqueous slurry of a monoalkali metal cyanurate such as monosodium cyanurate, chlorine gas, and either an alkali metal hypochlorite or hypochlorous acid. Reaction conditions for producing polychloroisocyanuric acid by these progresses include temperatures in the range of about $-5°$ to about $45°$ C. and a pH of from about 3 to about 4.5. The depressants described hereinabove may be added to the reaction mixture in any suitable manner. For example, they may be added directly or introduced into the reaction mixture in the aqueous slurry of the cyanuric compound or in a solution of hypochlorous acid or an alkali metal hypochlorite, if these are employed.

After this reaction, the polychloroisocyanuric acids, which are in the reaction mixture as particles of a crystalline solid are separated, washed and dried. During processing, a reaction slurry is formed, from which the particles of polychloroisocyanuric acid are separated and dried. Where the separation is done by filtering, the washed crystalline particles produced usually contain considerable amounts of water which both increases the separation time and the amount of heat required to dry the product. Further, current manufacturing processes tend to leave a small residue of salt impurity in the product which complicates the compounding of the dried material into the finished commercial products in which it is used.

The foam depressant technique described by Wojtowicz et al. above both reduces significantly the tendency of the reaction to foam, and improves the filterability of the final product. However, it is found that the polychloroisocyanuric acid filter cake still retains as much as 8 to 10 percent water and over 500 parts per million of sodium chloride. Such a quantity of moisture in the filter cake can cause product bridging after the cake discharge because moist product tends to pack and form a nonflowing cohesive mass. In practice, bridging must be recognized immediately before a process upset occurs due to loss of product downstream and backup of product into the filter.

In another process described in U.S. Pat. No. 3,142,647 issued July 28, 1964 to Glasgow, the filtered particles of polychloroisocyanuric acid are further bathed and coated with a 25–75 percent solution of a sodium alkyl aryl sulfonate rewetting agent. When dried, this coating acts to promote rapid dispersion of the particles when they are used in dry mixed detergents for automatic dishwashers and similar uses.

It is an object of the present invention to provide a process to produce a polychloroisocyanuric acid product having a lower residual water and salt content after filtration.

It is a further object of the present invention to provide a process for producing a polychloroisocyanuric acid product having improved drying properties.

Briefly, these objects are achieved in accordance with the process of this invention by adding between about 50 and about 500 parts per million of a surfactant wetting agent with about 100 to about 200 parts per million being preferred to the water used to wash the filter cake after it has been separated from the reaction mass. When this is done, it is found that both the residual water content and level of salt impurity in the cake are reduced from between about 20 to about 40 percent.

These and other objects of the subject invention will become apparent from the following description and the appended claims.

Foam depressants as described herein are members of a broad class of materials known generally as surfactants. Other materials in this class are widely used in industry as wetting agents. Such agents are materials adapted to improve the contact of a solvent with a dry solute so as to enhance the ability of the solute to absorb the solvent or to dissolve or disperse in it.

It has been found that the filter cake moisture can be significantly reduced by washing the cake with a dilute aqueous solution of a wetting agent. When this is done, the filter cake tends to retain less moisture than ordinarily occurs with a water wash so that a more flowable product results. As a result, the evaporative load in the drying section is significantly reduced. It is still further found that the dried cake has a lower salt content than normally washed cake.

For this use, the preferred operating concentration ranges in the wash water for the surfactant are fairly low, generally in the range of about 50 to about 500 parts per million with greatest sodium removal being seen at the higher concentration. However, care should be taken not to add too much surfactant so as to keep foaming to a minimum but the optimum concentration depends to a great extent on the particular surfactant material actually used. With an alkoxylated alkyl alcohol surfactant, the preferred operating concentration range is in the range of about 100 to about 200 parts per million.

Further while the process of this invention may be employed with conventionally produced polyisocyanuric acid particles, its use with the improved product produced by the method of Wojtowicz et al. is especially efficacious and is preferred.

A surfactant is defined as being an organic compound and encompasses in the same molecule two dissimilar structural groups, e.g., a "hydrophilic" water soluble and a "hydrophobic" water insoluble moiety. It is found that the composition, solubility properties, location and relative sizes of these dissimilar groups in relation to the overall molecular structural configuration all interact to determine the surfactant properties.

Surfactants are classified on the basis of their hydrophilic or water solubilizing groups into four separate categories: anionics, non-ionic, cationics, and amphoterics. Anionic groups include carboxylates, sulfonates, sulfates, and phosphates; non-ionic groups include hydroxyls which are usually polyalkoxylated terminated by polyoxyethylene groups, polyoxypropylene groups or block mixtures thereof, and cationic groups include primary, secondary, and tertiary amines and quaternary ammonium groups. Amphoteric surfactants are solubilized by some combination of anionic and cationic moieties; non-ionic groups may also be part of the amphoteric molecule. In addition to these primary solubilizing groups, other structural units may contribute to the hydrophilic tendencies of these molecules, e.g., ester linkages and amide linkages. The hydrophobic moieties are almost invariably hydrocarbon or halogen substituted hydrocarbon groups with olefin linkages being found to be less hydrophobic than single carbon-to-carbon bonds.

Correlation of functional properties with molecular structures has resulted in the identification of both strong wetting and strong detergent structures in surfactant materials. It is found that the hydrophilic group of strong wetting agents is located in the middle of the hydrophobic chain or at the central branching point if the molecule contains two or more chains. Where wetting is involved, representative examples are found in all four surfactant categories and while wetting efficiency is not simply related to the surface tension lowering properties of these surfactants, aqueous solutions of strong wetting agents characteristically have low surface tensions.

Examples of hydrophobic/hydrophilic combinations which can be used for the purpose of this invention include:

(1) Alkali metal dialkyl sulfosuccinates

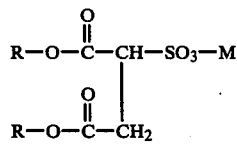

where M is sodium or potassium and R is a linear or branched alkyl chain having between about 5 and about 10 carbon atoms;

(2) Sodium alkyl naphthalene sulfonates

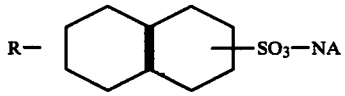

where R is a linear or branched alkyl chain having between about 3 and about 10 carbon atoms;

(3) Sodium N acyl N alkyltaurates

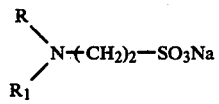

where R is an alkyl group having from between about 1 and about 3 carbon atoms or a cyclohexyl group with cyclohexyl groups being preferred; and R' is an acyl group having between about 10 and about 16 carbon atoms;

(4) Sodium alkyl sulfates:

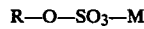

where R is a linear or branched chain alkyl group having between about 10 and about 18 carbon atoms and where M is sodium, ammonium, diethanolamino or triethanolamino;

(5) Sulfated esters derived from oleic or ricinoleic acids of the general formula

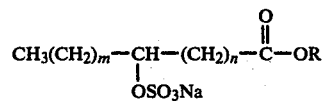

where m and n are linear alkyl carbon chains having between about 5 and about 10 carbon atoms and R is ethyl, propyl, butyl, or amyl;

(6) Sulfoxylated alkyl phenols

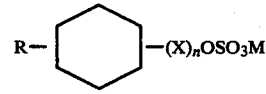

where R is a linear or branched alkyl chain having from between 8 and about 16 carbon atoms, X is ethoxy ($-CH_2-CH_2-O$) propoxy, ($CH_2-CH_2-CH_2-O-$) or a block mixture of the two said block mixture being a sequential alternation of ethoxy and propoxy groups along the phenolic chain, n is from about 3 to about 6, and M is sodium, ammonium, or triethanolamino;

(7) Ethoxylated alkyl phenols

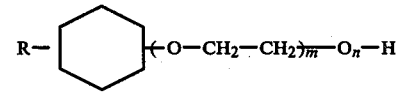

where R is a linear or branched chain group having between 8 to about 12 and n ranges from about 2 to about 30 with about 5 to about 15 being preferred;

(8) Alkoxylated alkyl phenols of the general formula

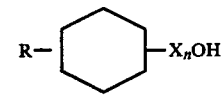

where R is a linear or branched chain group having between 8 to about 12 and X is a random or block mixture of ethoxy ($O-CH_2-CH_2$) and propoxy $(-O-CH_2-CH_2-CH_2-)$ groups where n is the combined number of ethoxy and propoxy groups with the number of ethoxy groups being between about 2 and about 15 and the number of propoxy groups being between about 2 and about 30 with a total for n of about 5 to about 15 being preferred;

(9) Ethoxylated aliphatic alcohols

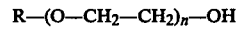

where R is a linear or branched chain alkyl group having between about 10 and about 18 carbon atoms, with about 12 to about 15 being preferred and where n, the number of ethoxy groups, ranges from about 1 to about 50, with about 5 to about 15 being preferred;

(10) Alkoxylated aliphatic alcohols

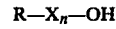

where R is a linear or branched chain alkyl group having between about 12 and about 18 carbon atoms, with about 5 to about 15 being preferred, X is a random or block mixture of ethoxy and propoxy groups and where n is the combined number of ethoxy and propoxy groups with the number of ethoxy groups being between about 2 and about 15 and the number of propoxy groups being between about 2 and about 30 with a total for n of about 5 to about 15 being preferred; and

(11) Alkoxylated glycols comprised of a block mixture of polyethylene glycol having a total molecular weight of between about 100 and about 6000 and polypropylene glycol having a total molecular weight from about 1000 to about 9000 for a gross molecular weight up to about 15,000, with surfactants of the sodium dialkyl sulfosuccinate and alkoxylated alkyl phenolic types being preferred for this application.

Adding a surfactant wetting agent to the rinse water, as disclosed herein, does not impose any special process modifications insofar as either rinsing or drying of the particles of the polyisocyanuric acid product.

The efficacy of the process of this invention is shown in the following examples.

EXAMPLE 1

About 300 cc of a well-stirred slurry comprised of about 10 percent by weight of trichloroisocyanuric acid, as prepared by the method of Wojtowicz et al in U.S. Pat. No. 4,220,768, supra, in water and having a gross density of about 1.11 was poured into a 4-inch diameter laboratory vacuum filter. The quantity of slurry used was equivalent to about 1.72 gallons of slurry/ft.$^2$ of filter area. About 3-4 seconds was required for the filtrate to pass through, leaving a residual moist cake of about 0.25 to about 0.3 inches thick. Such a thickness is about equal to that obtained in a plant operational vacuum filter used for this product. The cake was maintained under vacuum for an additional 12-15 seconds after which it was washed with a pressure spray of a solution containing about 125 ppm of an ethoxylated aliphatic alcohol surfactant (Olin Poly-Tergent ®J-200) in the wash water, created by a 1/8 K7.5 Flowjet ® spray nozzle at an application rate of about 0.097 gallons/ft.$^2$ and a temperature of about 25° C. for about 2 seconds. The washed, moist cake was then vacuum dried for an additional 30 seconds. It was found that the moisture in the cake was about 5.84 percent and the sodium content was about 347 ppm. No problem with foaming during or after the wash was observed.

EXAMPLE 2

The method of Example 1 was repeated with a wash surfactant concentration of about 250 ppm. While it was found that the sodium content of the moist cake was lowered to about 230 ppm, there was some level of foaming in the filtrate.

COMPARATIVE EXAMPLE

The method of Example 1 was repeated, but with a plain water wash. The moist cake contained about 8.22 percent water and 556 ppm sodium.

This invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

We claim:

1. In a process for the production of polychloroisocyanuric acid by the reaction of chlorine gas with a cyanuric compound selected from the group consisting of cyanuric acid, alkali metal cyanurates and alkaline earth metal cyanurates in a reaction mixture, and recovering said polychloroisocyanuric acid from said reaction mixture, said recovery comprising filtration to produce a filter cake, washing said cake with water, and drying said cake, the improvement which comprises adding a foam depressant selected from the group consisting of ethoxylated alcohols, alkoxylated alcohols and alkali metal salts of esters of dicarboxylic acids to said reaction mixture in an amount of between about 5 and about 500 ppm and further adding a surfactant wetting agent to said wash water selected from the group consisting of alkali metal dialkyl sulfosuccinates, sodium alkyl naphthalene sulfonates, sodium N acyl N alkyltaurates, sodium alkyl sulfates, sulfated ester, sulfoxylated alkyl phenols, ethoxylated alkyl phenols, alkoxylated alkyl phenols, ethoxylated alkyl alcohols, alkoxylated aliphatic alcohols and alkoxylated glycols.

2. In a process for the production of polychloroisocyanuric acid by the reaction of chlorine gas with a cyanuric compound selected from the group consisting of cyanuric acid, alkali metal cyanurates and alkaline earth metal cyanurates in a reaction mixture and recovering said polychloroisocyanuric acid from said reaction mixture, said recovery comprising filtration to produce a filter cake, washing said cake with water, and drying said cake, the improvement which comprises adding a surfactant wetting agent to said wash water selected from the group consisting of alkali metal dialkyl sulfosuccinates, sodium alkyl naphthalene sulfonates, sodium N acyl N alkyltaurates, sodium alkyl sulfates, sulfated ester, sulfoxylated alkyl phenols, ethoxylated alkyl phenols, alkoxylated alkyl phenols, ethoxylated alkyl alcohols, alkoxylated aliphatic alcohols and alkoxylated glycols.

3. The process of claim 1 or claim 2 wherein said surfactant wetting agent is an ethoxylated alkyl alcohol having the formula

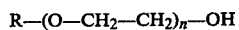

where R is a linear branched chain alkyl group having from between about 10 to about 18 carbon atoms and n, the number of ethoxy groups, ranges from about 1 to about 50.

4. The process of claim 3 wherein R is an aliphatic group having from between about 12 and about 15 carbon atoms and n ranges between about 5 and about 15.

5. The process of claim 1 or claim 2 wherein said surfactant wetting agent is an alkali metal dialkyl sulfosuccinate having the general formula

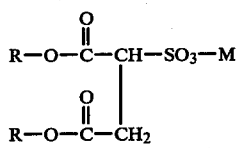

where M is sodium or potassium and R is a linear or branched alkyl chain having between about 5 and about 10 carbon atoms.

6. The process of claim 5 wherein M is sodium.

7. The process of claim 3 wherein the concentration of said surfactant wetting agent in said wash water is between about 50 and about 500 ppm.

8. The process of claim 7 wherein said surfactant concentration is between about 100 and about 200 ppm.

9. The process of claim 5 wherein the concentration of said surfactant wetting agent in said wash water is between about 50 and about 500 ppm.

10. The process of claim 9 wherein said surfactant concentration is between about 100 and about 200 ppm.

* * * * *